United States Patent [19]

Stelzer et al.

[11] Patent Number: 5,925,785
[45] Date of Patent: *Jul. 20, 1999

[54] SECONDARY AND TERTIARY PHOSPHINES AND PROCESSES FOR THEIR PREPARATION

[75] Inventors: Othmar Stelzer; Oliver Herd, both of Wuppertal; Norbert Weferling, Hürth, all of Germany

[73] Assignee: Celanese GmbH, Frankfurt am Main, Germany

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/821,715

[22] Filed: Mar. 20, 1997

Related U.S. Application Data

[63] Continuation of application No. 08/622,939, Mar. 27, 1996, abandoned, which is a continuation of application No. 08/276,439, Jul. 18, 1994.

[30] Foreign Application Priority Data

Jul. 31, 1993 [DE] Germany .................. 43 25 816

[51] Int. Cl.⁶ .................................................. C07F 9/02
[52] U.S. Cl. ................................ 562/35; 562/45; 546/21; 568/13
[58] Field of Search ................. 546/21; 562/45, 562/35; 568/13

[56] References Cited

U.S. PATENT DOCUMENTS 4,483,801 11/1984 Sabot .................... 260/505 C
5,268,479 12/1993 Stelzer et al. .................. 546/21

FOREIGN PATENT DOCUMENTS 0 307 717 3/1989 European Pat. Off. .
2 262 284 6/1993 United Kingdom .

OTHER PUBLICATIONS

Angewandte Chemie, 105:1097–1099, (Jul., 1993); English Translation=Angewandte Chemie, International Edition (1993) 32:1058–1059 (copy enclosed).

*Primary Examiner*—Paul J. Killos
*Assistant Examiner*—Jean F Vollano
*Attorney, Agent, or Firm*—Connolly and Hutz

[57] ABSTRACT

The invention relates to secondary and tertiary phosphines of the formula

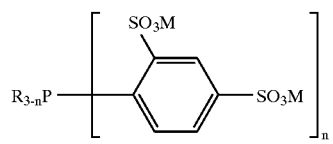

in which R is hydrogen, an aryl or benzyl group or a straight-chain or branched alkyl group, n is 1 or 2 and M is potassium or sodium.

These phosphines are prepared by reacting either alkali metal salts of fluorobenzene-2,4-disulfonic acid with phosphine or with primary or secondary phosphines, or secondary phosphines of the type $HP[C_6H_3\text{-}2,4\text{-}(SO_3M)_2]_2$ with a compound RX in which R is an alkyl, aryl or benzyl group and X is a halogen, in an aprotic solvent in the presence of at least stoichiometric quantities of a solid, powdered alkali metal hydroxide at temperatures of from 0 to 100° C.

9 Claims, No Drawings

SECONDARY AND TERTIARY PHOSPHINES AND PROCESSES FOR THEIR PREPARATION

This application is a continuation of application Ser. No. 08/622,939 filed on Mar. 27, 1996, now abandoned, which in turn is a continuation of Ser. No. 08/276,439 filed Jul. 18, 1994.

The present invention relates to secondary and tertiary phosphines and processes for their preparation.

Water-soluble phosphines, for example the trisodium salt of triphenylphosphine-tris-m-sulfonic acid, have been employed in recent years as ligands in catalysts for the oxo synthesis in a two-phase system comprising organic solvent and water. These water-soluble phosphines were previously prepared by reacting triphenylphosphine with oleum and neutralizing the reaction mixture using sodium hydroxide solution, although this results in mixtures of phosphines, phosphine oxides and phosphine sulfides with various degrees of sulfonation, which require complex separation by means of precipitation and extraction procedures or gel permeation chromatography. Phosphines having disulfonated aromatic radicals cannot be obtained by reacting triphenylphosphine with oleum.

The invention relates specifically to secondary and tertiary phosphines of the formula

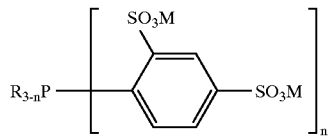

in which R is hydrogen, an aryl or benzyl group or a straight-chain or branched alkyl group, n is 1 or 2 and M is potassium or sodium.

These phosphines are prepared by reacting either alkali metal salts of fluorobenzene-2,4-disulfonic acid with phosphine or with primary or secondary phosphines in an aprotic solvent in the presence of at least stoichiometric quantities of a solid, powdered alkali metal hydroxide at temperatures of from 0 to 100° C., a reaction which can be carried out at pressures of up to 10 bar, preferably up to 2 bar, or reacting a secondary phosphine of the type $HP[C_6H_3\text{-}2,4\text{-}(SO_3M)_2]_2$ with a compound RX in which R is an alkyl, aryl or benzyl group and X is a halogen, in an aprotic solvent in the presence of at least stoichiometric quantities of a solid, powdered alkali metal hydroxide at temperatures of from 0 to 100° C.

The processes for the preparation of these phosphines may have the additional, optional features that a) the solvent used is dimethyl sulfoxide;
b) the solvents used are glycol ethers;
c) the alkali metal hydroxide used is potassium hydroxide.

The secondary and tertiary phosphines according to the invention can be used as intermediates in the synthesis of pharmaceuticals and crop protection agents.

The potassium salt of fluorobenzene-2,4-disulfonic acid can be obtained in accordance with the following working procedure: 93.3 ml (1 mol) of fluorobenzene were added dropwise to 200 ml of chlorosulfonic acid over one hour. When the evolution of hydrogen chloride had ceased, the reaction mixture was stirred at room temperature for 2 hours and then poured onto 300 g of ice. It was extracted with chloroform, and the organic phase was washed with 50 ml of water and saturated sodium hydrogen carbonate solution. Distillation of the organic phase in vacuo gave 175 g (90% of theory) of p-$FC_6H_4SO_2Cl$ (boiling point: 86 to 88° C. at 0.1 mbar; melting point: 35 to 38° C.).

30 g (0.15 mol) of p-$FC_6H_4SO_2Cl$ were heated with 25 ml of oleum (17%) at 200° C. for 5 hours. The reaction mixture was then poured onto 250 g of ice, and 20 g (0.14 mol) of potassium carbonate were added. The resulting crude product was recrystallized once from water.

Yield: 48.0 g (87% of theory)
$C_6H_3FK_2O_6S_2 \cdot 2H_2O$ (M=368.4) calc.: C 19.56% H 1.92% found: C 19.31% H 1.71%
$^{19}F$ NMR ($CCl_3F$): −119.0; $^1H$ NMR: H3 8.3; dd, J(HF)=6.6; J(HH)=2.4; H5 8.1 ddd, J(HF)=4.6, J(HH)=2.4, 8.6; H6 7.5, dd, J(HF)=9.9, J(HH)=8.6; $^{13}C[^1H]$ NMR: C1 161.2, d (255.4); C2 ($SO_3K$) 131.4, d (17.6); C3 132.2, d (9.8); C4 ($SO_3K$) 140.0; C5 127.2, d (1.9); C6 118.8 (23.3).

EXAMPLE 1

Preparation of $HP[C_6H_3\text{-}2,4\text{-}(SO_3K)_2]_2$ 12 g of solid, powdered potassium hydroxide (85%; 0.18 mol) and 20 g of molecular sieve (3 Å) were suspended in 60 ml of dimethyl sulfoxide. The suspension was saturated with $PH_3$ at an overpressure of 0.1 bar, with formation of a pale yellow solution. 20 g (60 mmol) of the potassium salt of fluorobenzene-2,4-disulfonic acid were added to this solution over the course of one hour, and the mixture was subsequently stirred at 60° C. for 12 hours, the $PH_3$ overpressure of 0.1 bar being maintained by supplementary addition. The resulting dark red solution was neutralized with aqueous hydrofluoric acid and 200 ml of ethanol were added. The resulting precipitate was filtered off, washed with three times 30 ml of methanol and subsequently recrystallized from water.

Yield: 11.3 g (57% of theory)
$C_{12}H_7K_4O_{12}PS_4 \cdot 2H_2O$ (M=694.8) calc.: C 20.74 H 1.60 found: C 21.14 H 1.67
$^{31}P$ NMR: −46.5, d (244.9); $^{13}C[^1H]$ NMR (TMS): C1 (P)137 8. d (22.9); C2 ($SO_3K$) 147.6 d (19.3); C3 138.7; C4 ($SO_3K$) 144.2; C5 128.7; C6 124.8, d (2.5); $^1H$ NMR; H3 8.3, dd. J(PH)=2.3, J(HH)=1.7; H5 7.7, dd, J(HH)=1.7, 8.0; H6 7.4, dd, J(HH)=8.0, J(PH)=3.9; H(PH) 5.7, d (239.1).

EXAMPLE 2

Preparation of $C_6H_5P[C_6H_3\text{-}2,4\text{-}(SO_3K)_2]_2$ 2.8 g (25 nmol) of phenylphosphine were dissolved in 50 ml of dimethyl sulfoxide, and 3.3 g (50 mmol) of solid, powdered potassium hydroxide were added. A suspension of 16.6 g (50 mmol) of $F\text{-}C_6H_3\text{-}2,4\text{-}(SO_3K)_2$ in 50 ml of dimethyl sulfoxide was added to this solution over the course of one hour. The reaction mixture was subsequently stirred at 60° C. for 12 hours. Addition of 150 to 200 ml of ethanol resulted in a white precipitate which was filtered off over an inverse frit. The precipitate isolated by filtration was washed with three times 30 ml of methanol and finally recrystallized from water.

Yield: 12.1 g (60% of theory)
$C_{18}H_{11}K_4O_{12}PS_4 \cdot 4H_2O$ (M=806.9) calc.: C 26.79 H 2.37 found: C 26.98 H 2.27
$^{31}P[^1H]$ NMR: −13.2

EXAMPLE 3

Preparation of $C_6H_5P[C_6H_3\text{-}2,4\text{-}(SO_3K)_2]_2$ 6.6 g (100 mmol) of solid, powdered potassium hydroxide were added to a solution of 2.8 g (25 mmol) of phenylphosphine in 150 ml of ethylene glycol dimethyl ether Following addition of 16.6 g (50 mmol) of the potassium salt of fluorobenzene-2,4-disulfonic acid, the reaction mixture was stirred at 80° C. for 36 hours. The residue which remained after stripping off the solvent in vacuo (0.1 mbar, 20–50° C.) was recrystallized with three times 20 ml of water.

Yield: 4.0 g (20% of theory)

EXAMPLE 4

Preparation of $(C_6H_5)_2P[C_6H_3-2,4-(SO_3K)_2]$ 4.7 g (25 mmol) of diphenylphosphine were dissolved in 50 ml of dimethyl sulfoxide, and 1.6 g (25 mmol) of solid, powdered potassium hydroxide were added. A suspension of 8.3 g (25 mmol) of $F-C_6H_3-2,4-(SO_3K)_2$ in 50 ml of dimethyl sulfoxide was added to this solution over the course of one hour, and the reaction mixture was subsequently stirred at 60° C. for 12 hours. Following addition of 200 ml of ethanol, a white precipitate was obtained which was isolated by filtration, washed with three times 30 ml of methanol and subsequently recrystallized from water.

Yield: 7.7 g (58% of theory)

$C_{18}H_{13}K_2O_6PS_2 \cdot 2H_2O$ (M=534.6) calc.: C 40.44 H 3.21 found: C 40.89 H 3.58

$^{31}P[^1H]$ NMR: −10.8

EXAMPLE 5

Preparation of $C_5NH_4-P[C_6H_3-2,4-(SO_3K)_2]_2$ 1.2 g (18 mmol) of solid, powdered potassium hydroxide were added to a solution of 0.84 g (7.5 mmol) of 2-pyridylphosphine in 60 ml of dimethyl sulfoxide. Following addition of 4.98 g (15 mmol) of the potassium salt of fluorobenzene-2,4-disulfonic acid, the reaction mixture was stirred at 20–60° C. for 12 hours. Addition of 50 ml of ethanol resulted in a white precipitate which was filtered off and washed with three times 30 ml of methanol, and was finally recrystallized from 20 ml of water.

Yield: 2 g (36% of theory)

$^{31}P[^1H]$ NMR: −13.0; $^{13}C[^1H]$ NMR (TMS): C1 (P) 138.1, d (26.0): C2 ($SO_3K$) 148.9, d (25.9); C3 137.7; C4 ($SO_3K$) 144.9; C5 128.9; C6 125.8, d (4.1); C7 (P, N) 162.9, d (6.2); C8 130.7, d (13.0); C9 138.5, d (1.9); C10 124.9; C11 (N) 150.6, d (13.9).

EXAMPLE 6

0.4 g (4.3 mmol) of monofluorobenzene was added to a solution of 3.0 g (4.3 mmol) of $HP[C_6H_3-2,4-(SO_3K)_2]_2$ in 60 ml of dimethyl sulfoxide, and 0.3 g of solid, powdered KOH was added to the mixture. The reaction mixture was then stirred at 60° C. for 12 hours. Addition of 100 ml of ethanol resulted in a white precipitate which was filtered off over an inverse frit. The precipitate isolated by filtration was washed with three times 30 ml of methanol and recrystallized from water.

Yield: 1.6 g (45% of theory)

$C_{18}H_{11}K_4O_{12}PS_4 \cdot 4H_2O$ (M=806.9) calc.: C 26.79 H 2.37 found: C 26.98 H 2.27

$^{31}P[^1H]$ NMR: −13.2

EXAMPLE 7

1.2 g (8.6 mmol) of mono-n-butyl bromide were added to a solution of 6.0 g (8.6 mmol) of $HP[C_6H_3-2,4-(SO_3K)_2]_2$. 0.6 g (9.5 mmol) of solid, powdered potassium hydroxide was introduced into this mixture over the course of one hour. The reaction mixture was then stirred at 60° C. for 12 hours. Addition of 100 ml of ethanol resulted in a white precipitate which was filtered off over an inverse frit. The precipitate isolated by filtration was washed with three times 30 ml of methanol and recrystallized from water.

Yield: 2.6 g (38% of theory)

$C_{16}H_{15}K_4O_{12}PS_4 \cdot 4H_2O$ (M=787.0) calc.: C 24.42 H 2.95 found: C 24.74 H 2.94

$^{31}P[^1H]$ NMR: −23.9

EXAMPLE 8

0.26 g (1.5 mmol) of benzyl bromide were added to a solution of 1.04 g (1.5 mmol) of the secondary phosphine $HP[C_6H_3-2,4-(SO_3K)_2]_2$ in 40 ml of dimethyl sulfoxide, and 0.11 g (1.7 mmol) of solid, powdered potassium hydroxide was added in portions to the mixture. The reaction mixture was then stirred at 20° C. for 12 hours. Addition of 100 ml of ethanol resulted in a white precipitate which was filtered off over an inverse frit. The precipitate isolated by filtration was recrystallized from 50 ml of hot methanol.

Yield: 0.55 g (49% of theory)

$^{31}P[^1H]$ NMR: −16.0; $^{13}C[^1H]$ NMR (TMS): C1 (P) 139.8, d (31.1); C2 ($SO_3K$) 148.5, d (25.5); C3 136.1; C4 ($SO_3K$) 144.4; C6 125.9, d (3.8); C7 (i, Bz) 139.1, d (10.3); 130.3, d (8.6); 129.7; 128.7; 127.3, d (2.4) [C5, C8 (0, Bz), C9 (m, Bz), C10 (p, Bz)]; $CH_2$ 34.3, d (15.8).

We claim:

1. A process for the preparation of a secondary or tertiary phosphine of the formula

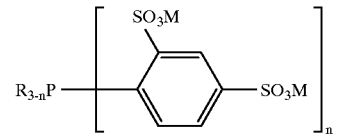

in which R is hydrogen, an aryl group, a benzyl group, a straight-chain alkyl group or a branched alkyl group, n is 1 or 2 and M is potassium or sodium, which comprises reacting an alkali metal salt of fluorobenzene-2,4-disulfonic acid with phosphine or a primary or secondary phosphine in an aprotic solvent in the presence of at least stoichiometric quantities of a solid, powdered alkali metal hydroxide at temperatures of from 0 to 100° C.

2. The process as claimed in claim 1, wherein the reaction is carried out at pressures of up to 10 bar.

3. The process as claimed in claim 2, wherein the pressure is up to 2 bar.

4. The process as claimed in claim 1, wherein the solvent used is dimethyl sulfoxide.

5. The process as claimed in claim 1, wherein the solvent used is a glycol ether.

6. The process as claimed in claim 1, wherein the alkali metal hydroxide used is potassium hydroxide.

7. The process as claimed in claim 3, wherein the solvent used is dimethyl sulfoxide.

8. The process as claimed in claim 3, wherein the solvent used is a glycol ether.

9. The process as claimed in claim 3, wherein the alkali metal hydroxide used is potassium hydroxide.

* * * * *